United States Patent
Shudo et al.

(10) Patent No.: US 9,446,095 B2
(45) Date of Patent: Sep. 20, 2016

(54) SOLID COMPOSITION CONTAINING WHEAT ALBUMIN AND ALANINE OR A SALT THEREOF

(71) Applicant: KAO CORPORATION, Chuo-ku (JP)

(72) Inventors: Aiko Shudo, Sumida-ku (JP); Nobuteru Ishizuka, Sumida-ku (JP)

(73) Assignee: KAO CORPORATION, Chuo-ku (JP)

( * ) Notice: Subject to any disclaimer, the term of this patent is extended or adjusted under 35 U.S.C. 154(b) by 0 days.

(21) Appl. No.: 14/766,933

(22) PCT Filed: Feb. 13, 2014

(86) PCT No.: PCT/JP2014/053329
§ 371 (c)(1),
(2) Date: Aug. 10, 2015

(87) PCT Pub. No.: WO2014/126152
PCT Pub. Date: Aug. 21, 2014

(65) Prior Publication Data
US 2015/0374782 A1    Dec. 31, 2015

(30) Foreign Application Priority Data

Feb. 15, 2013   (JP) .................................. 2013-027742

(51) Int. Cl.
| | | |
|---|---|---|
| *A23J 3/18* | (2006.01) | |
| *A23L 1/305* | (2006.01) | |
| *A61K 38/16* | (2006.01) | |
| *A23L 1/03* | (2006.01) | |
| *A23L 1/10* | (2006.01) | |
| *A61K 9/00* | (2006.01) | |
| *A61K 9/20* | (2006.01) | |
| *A61K 9/68* | (2006.01) | |

(52) U.S. Cl.
CPC ............ *A61K 38/168* (2013.01); *A23L 1/0325* (2013.01); *A23L 1/1008* (2013.01); *A23L 1/3051* (2013.01); *A23L 1/3055* (2013.01); *A61K 9/0056* (2013.01); *A61K 9/0058* (2013.01); *A61K 9/2009* (2013.01); *A61K 9/2013* (2013.01); *A23V 2002/00* (2013.01); *A23V 2200/16* (2013.01)

(58) Field of Classification Search
None
See application file for complete search history.

(56) References Cited

U.S. PATENT DOCUMENTS

| | | | |
|---|---|---|---|
| 6,339,104 B1 | 1/2002 | Nishiguchi et al. | |
| 9,259,454 B2 * | 2/2016 | Shudo ................... | A23L 1/3055 |
| 2002/0193342 A1 * | 12/2002 | Hamman .............. | A23L 1/2367 514/53 |
| 2009/0053378 A1 * | 2/2009 | Prakash ................. | A23L 1/236 426/548 |
| 2013/0156503 A1 | 6/2013 | Obermeyer | |
| 2013/0156923 A1 * | 6/2013 | Shudo ................... | A23L 1/3055 426/548 |
| 2014/0213503 A1 | 7/2014 | Shudo et al. | |

FOREIGN PATENT DOCUMENTS

| | | |
|---|---|---|
| CN | 1515185 | 7/2004 |
| JP | 8-157356 A | 6/1996 |
| JP | 10-99023 | 4/1998 |
| JP | 11-189516 A | 7/1999 |
| JP | 2006-212020 A | 8/2006 |
| JP | 2006-223293 A | 8/2006 |
| JP | 2007-330124 A | 12/2007 |
| JP | 2010-173962 A | 8/2010 |
| JP | 2013-74869 A | 4/2013 |
| JP | 2013-74869 A | 4/2013 |
| JP | 2013-87062 A | 5/2013 |
| WO | 99/53914 A1 | 10/1999 |

OTHER PUBLICATIONS

International Preliminary Report on Patentability and Written Opinion issued Aug. 27, 2015 in PCT/JP2014/053329.
T. Kodama, et al., "Effects of single and long-term administration of wheat albumin on blood glucose control: randomized controlled clinical trials," European Journal of Clinical Nutrition (2005), vol. 59, No. 3, pp. 384-392.
Kazuki Nukii, et al., "Effects of Single Administration of Wheat Albumin by Hard Capsules on Blood Glucose Control," Pharmacology and Treatment, vol. 36, No. 8 (2008) (11 pages, with English abstract and partial English translation).
International Search Report issued Apr. 15, 2014 in PCT/JP2014/053329 filed Feb. 13, 2014.

* cited by examiner

*Primary Examiner* — Jeffrey E Russel
(74) *Attorney, Agent, or Firm* — Oblon, McClelland, Maier & Neustadt, L.L.P.

(57) ABSTRACT

Provided is a solid composition which has reduced bad taste and offensive odor and provides good taste and flavor, while containing wheat albumin at a high concentration. A solid composition comprising the following components (A) and (B): (A) wheat albumin, and (B) alanine or a salt thereof, wherein a mass ratio of a content of the 0.19-wheat albumin (a) in the solid composition to a content of the alanine or a salt thereof in terms of alanine (b) in the solid composition, [(a):(b)], is from 250:1 to 10:1.

20 Claims, No Drawings

SOLID COMPOSITION CONTAINING WHEAT ALBUMIN AND ALANINE OR A SALT THEREOF

FIELD OF THE INVENTION

The present invention relates to a solid composition comprising wheat albumin.

BACKGROUND OF THE INVENTION

Recently, the number of patients suffering from glucose metabolic disorders represented by obesity and type II diabetes mellitus (hyperglycemia) has been increasing due to, for example, changes in dietary habits.

In general, the blood glucose level is increased after eating, in particular, after ingestion of a diet containing carbohydrates, and thereby insulin is secreted by pancreatic β-cells. Insulin acts on muscle, liver, adipose tissue, etc. and promotes the intake of sugar into cells, to thereby suppress an acute increase in blood glucose level after eating. If the postprandial blood glucose level remains high because of a decrease in insulin sensitivity (insulin resistance), the pancreas secretes a large amount of insulin for suppressing the increase in blood glucose level. Furthermore, if such a condition continues for a long time, the pancreas is exhausted, the secretion of insulin from the pancreatic β-cells is decreased, and, ultimately, the mechanism of insulin action does not normally function, which causes, for example, type II diabetes mellitus.

The postprandial hyperglycemia symptoms associated with insulin resistance also appears in healthy individuals not suffering from diabetes mellitus and individuals suffering from borderline diabetes mellitus. The postprandial hyperglycemia symptoms are also known to cause or exacerbate, for example, obesity, hyperlipidemia, and arteriosclerosis, in addition to type II diabetes mellitus. Accordingly, from the viewpoints of health maintenance, decrease in the risk for onset of these symptoms and diseases and prevention thereof, it is very important to prevent the postprandial hyperglycemia symptoms.

Accordingly, many materials that can suppress an acute increase in blood glucose level and secretion of insulin after eating have been developed in recent years. One example of such materials is amylase inhibitors, and an amylase inhibitor derived from wheat is used in prevention or therapy for, for example, diabetes mellitus and obesity (Non Patent Document 1).

The endosperm of wheat contains about 10 to 15% of protein. It has been reported that albumin (water-soluble protein) occupying about 11% of the protein composition has an α-amylase inhibiting activity and physiological functions such as an action of suppressing a postprandial increase in blood glucose level and an action of improving insulin resistance (Non Patent Documents 1 and 2). In particular, wheat albumin having an electrophoretic mobility of 0.19 has a high α-amylase inhibiting activity and is therefore expected to be applied to a variety of foods.

It is believed that in order to express the physiological functions of the wheat albumin, it is effective to ingest wheat albumin having an electrophoretic mobility of 0.19 (hereinafter, also may be referred to as 0.19-wheat albumin) in an amount of 125 mg or more per meal all at a time (Non Patent Document 2). As health foods having effective amounts of wheat albumin blended therein, soups and hard capsules have been marketed. In addition, Patent Document 1 discloses tablets having 0.19-wheat albumin blended therein.

PATENT DOCUMENT (Patent Document 1) JP-A-2010-173962

NON PATENT DOCUMENT (Non Patent Document 1) Yakuri to Chiryo (Pharmacology and Therapeutics), 2008, Vol. 36, No. 8, pp. 761-765.
(Non Patent Document 2) European Journal of Clinical Nutrition, 2005, Vol. 59, pp. 384-392.

SUMMARY OF THE INVENTION

The present invention provides a solid composition comprising the following components (A) and (B):
(A) wheat albumin, and
(B) alanine or a salt thereof, wherein
a mass ratio of a content of 0.19-wheat albumin (a) in the solid composition to a content of the alanine or a salt thereof in terms of alanine (b) in the solid composition, [(a):(b)], is from 250:1 to 10:1.

DETAILED DESCRIPTION OF THE INVENTION

In order to ingest wheat albumin effortlessly and continuously for a long term, a solid composition which is a form enabling easy ingestion in a small amount at a time is advantageous.

The investigation by the present inventors, however, revealed that it is difficult to blend wheat albumin in a solid composition at a high concentration such that an effective amount of wheat albumin can be ingested by only ingesting a small amount of the composition once. That is, it was revealed that an increase in the concentration of wheat albumin causes bad taste and offensive odor derived from wheat albumin to make ingestion difficult from the viewpoint of taste and flavor.

Accordingly, the present invention provides a solid composition having reduced bad taste and offensive odor and providing good taste and flavor, while containing wheat albumin at a high concentration. Note that Patent Document 1 mentioned above does not describe at all improvement of bad taste, etc. of tablets containing wheat albumin.

The present inventors diligently studied to solve the above-mentioned problems and, as a result, found that inclusion of a specific amino acid in a solid composition containing wheat albumin can reduce bad taste and offensive odor characteristic to wheat albumin and provide good taste and flavor regardless of containing wheat albumin at a high concentration in the solid composition.

The present invention can provide a solid composition, which has reduced bad taste and offensive odor derived from wheat albumin and provides a good taste and flavor, though the composition contains wheat albumin at a high concentration.

The solid composition of the present invention allows ingestion of wheat albumin in an amount required for the physiological effect thereof by only ingesting a small amount of the composition once. Accordingly, the effect of the wheat albumin can be expected over a long time.

The wheat albumin (A) used in the present invention is a water-soluble protein belonging to an albumin family derived from the endosperm of wheat. In light of having a high α-amylase inhibiting activity, it is preferable that the wheat albumin includes much wheat albumin having an electrophoretic mobility of 0.19. Incidentally, herein, the term "electrophoretic mobility" refers to the mobility of a sample subjected to electrophoresis by using polyacrylamide gel in accordance with the method of Davis (Annals of the New York Academy of Science, 121, 404-427, 1964).

The wheat albumin mentioned above can be extracted from the endosperm of wheat. The wheat albumin can be extracted from wheat by, for example, the method of preparing an amylase inhibitor described in JP-A-9-172999.

In addition, commercially available products such as wheat albumin NA-1 (Nisshin Pharma Inc.) may be used.

The content of the wheat albumin (A) in the solid composition of the present invention is 10% by mass (hereinafter, simply referred to as "%") or more, preferably 20% or more, even more preferably 30% or more from the viewpoints of ingestion amount for effectively attaining the physiological effect and of an ingestion form which enables ingestion in a small amount at a time, and is 70% or less, preferably 60% or less, more preferably 55% or less, even more preferably 50% or less from the viewpoint of providing a good taste and flavor. Additionally, the content is from 10 to 70%, preferably from 20 to 70%, more preferably from 30 to 60%, even more preferably from 30 to 55%, even more preferably from 30 to 50%.

The content of 0.19-wheat albumin in the wheat albumin (A) is 10% or more, preferably 15% or more, more preferably 20% or more, even more preferably 25% or more from the viewpoint of ingestion amount for effectively attaining the physiological effect and is 60% or less, preferably 40% or less, more preferably 35% or less, even more preferably 31% or less from the viewpoint of industrial productivity. Additionally, the content is from 10 to 60%, preferably from 15 to 40%, more preferably from 20 to 35%, even more preferably from 25 to 31%.

A content of 0.19-wheat albumin (a) in the solid composition of the present invention is 2% or more, preferably 7% or more, more preferably 7.5% or more from the viewpoint of the ingestion amount for effectively attaining the physiological effect and is 18% or less, more preferably 15% or less, even more preferably 13% or less from the viewpoint of industrial productivity and providing a good taste and flavor. Additionally, the content is from 2 to 18%, preferably from 7 to 15%, more preferably from 7.5 to 13%.

The content of 0.19-wheat albumin (a) in the solid composition of the present invention can be measured by HPLC. For example, the method of measuring the content of 0.19-amylase inhibitor described in JP-A-9-172999 can be employed.

The solid composition of the present invention contains alanine or a salt thereof (B). The alanine may be D-alanine or L-alanine, or may be DL-alanine as a mixture of the isomers.

Examples of the salt of alanine include acid addition salts formed with inorganic acids such as hydrochloric acid, hydrobromic acid, sulfuric acid, phosphoric acid, and nitric acid or organic acids such as acetic acid, propionic acid, succinic acid, glycolic acid, lactic acid, malic acid, tartaric acid, citric acid, maleic acid, fumaric acid, methanesulfonic acid, benzenesulfonic acid, p-toluenesulfonic acid, and ascorbic acid; salts formed with an inorganic base such as alkali metals including sodium and potassium, alkaline earth metals including calcium, or ammonium; and salts formed with organic bases such as methylamine, diethylamine, triethylamine, ethylenediamine, monoethanolamine, diethanolamine, and triehanolamine.

A content of the alanine or a salt thereof (B) in the solid composition of the present invention is, in terms of alanine, preferably 0.02% or more, more preferably 0.04% or more, still more preferably 0.05% or more from the viewpoint of reducing the bad taste and offensive odor of wheat albumin, and preferably 2.5% or less, more preferably 1.2% or less, still more preferably 0.6% or less, still more preferably 0.2% or less from the viewpoint of suppressing the taste derived from the amino acid added.

The content of the alanine or a salt thereof (B) in the present invention includes alanine derived from other materials such as wheat albumin in addition to the alanine blended.

In the solid composition of the present invention, it is important that a mass ratio of a content of the 0.19-wheat albumin (a) in the solid composition to a content of the alanine or a salt thereof in terms of alanine (b) in the solid composition, [(a):(b)], is in the range from 250:1 to 10:1. The bad taste and offensive odor characteristic to wheat albumin can be reduced by adjusting the content of the 0.19-wheat albumin (a), based on the content of the alanine or a salt thereof in terms of alanine (b) defined as 1, to 250 or less, preferably 150 or less, more preferably 100 or less, still more preferably 95 or less, still more preferably 90 or less. Meanwhile, the taste of alanine or a salt thereof is suppressed and good balance in taste and flavor is provided by adjusting the content of the 0.19-wheat albumin (a), based on the content of the alanine or a salt thereof in terms of alanine (b) defined as 1, to 10 or more, preferably 20 or more, more preferably 30 or more, still more preferably 50 or more, still more preferably 75 or more.

The mass ratio of a content of the 0.19-wheat albumin (a) to a content of the alanine or a salt thereof in terms of alanine (b), [(a):(b)], is preferably from 150:1 to 20:1, more preferably from 100:1 to 30:1, still more preferably from 95:1 to 50:1, still more preferably from 90:1 to 75:1 from the viewpoints of reducing the bad taste and offensive odor characteristic to wheat albumin, suppressing the taste of alanine or a salt thereof, and providing good balance in taste and flavor.

The solid composition of the present invention preferably further contains a sugar alcohol having 6 to 12 carbon atoms (C) from the viewpoints of reducing the offensive odor derived from wheat albumin and reducing bad returning odor during/after ingestion. The bad returning odor herein is the bad odor returning from the esophagus during/after ingestion.

Examples of the sugar alcohol having 6 to 12 carbon atoms (C) used in the present invention include maltitol, sorbitol, lactitol, and mannitol. These sugar alcohols may be used alone or in combination of two or more.

Among them, maltitol, sorbitol, and lactitol are preferred, maltitol and/or sorbitol are more preferred, and maltitol is still more preferred from the viewpoint of reducing the offensive odor and bad returning odor characteristic to wheat albumin. The above-described sugar alcohol may be any of its anhydrides and hydrates.

A content of the sugar alcohol having 6 to 12 carbon atoms (C) in the solid composition of the present invention is preferably 10% or more and more preferably 20% or more from the viewpoint of reducing the offensive odor and bad returning odor characteristic to wheat albumin, and preferably 90% or less, more preferably 65% or less, still more preferably 60% or less, still more preferably 55% or less, still more 40% or less from the viewpoint of the form which enables ingestion in a small amount at a time. Furthermore, the content is preferably from 10 to 90%, more preferably from 20 to 65%, still more preferably from 20 to 60%, still more preferably from 20 to 55%, still more preferably from 20 to 40%. The content of the sugar alcohol having 6 to 12 carbon atoms (C) is in terms of its anhydride.

The content of the sugar alcohol can be measured by HPLC. For example, analysis by differential refractometry using an amino column is available (Shokumotsu Seni, Kiso to Oyo (Dietary Fiber, its Basis and Application), supervised by Japanese Association for Dietary Fiber Research, edited by Japanese Association for Dietary Fiber Research Editorial Committee, et al., written by Seiichiro Aoki, published by Dai-ichi Shuppan, Co., Ltd., in October 2008).

In the solid composition of the present invention, a content mass ratio of the sugar alcohol having 6 to 12 carbon atoms (C) to the wheat albumin (A), [(C)/(A)], is preferably 0.2 or more, more preferably 0.4 or more, still more preferably 0.5 or more, still more preferably 0.7 or more from the viewpoint of reducing the offensive odor or bad returning odor characteristic to wheat albumin, and preferably 10 or less, more preferably 7 or less, still more preferably 5 or less, still more preferably 2 or less, still more preferably 1.9 or less, still more preferably 1 or less from the viewpoint of the form which enables ingestion in a small amount at a time. The content mass ratio is preferably from 0.2 to 10, more preferably from 0.4 to 7, still more preferably from 0.4 to 5, still more preferably from 0.5 to 2, still more preferably from 0.7 to 1.9, still more preferably from 0.7 to 1.

In the solid composition of the present invention, a content mass ratio of the sugar alcohol having 6 to 12 carbon atoms (C) to the 0.19-wheat albumin (a), [(C)/(a)], is preferably 0.8 or more, more preferably 1.5 or more, even more preferably 2.5 or more from the viewpoint of reducing the offensive odor or bad returning odor characteristic to wheat albumin, and preferably 10 or less, more preferably 7.5 or less, even more preferably 5 or less, even more preferably 3.5 or less from the viewpoint of the form which enables ingestion in a small amount at a time.

Additionally, the solid composition of the present invention preferably further contains a carbonate (D) or a carbonate (D) and an organic acid (E). Combination of wheat albumin with a carbonate can suppress sticky texture and sticking to the mouth. Additionally, the wheat albumin is combined with carbonate and the organic acid to generate carbon dioxide gas. In spite of containing wheat albumin at a high concentration, the carbon dioxide gas generated can suppress sticky texture and sticking to the mouth and reduce the bad taste characteristic to wheat albumin to provide a solid composition having good texture, taste and flavor.

Examples of the carbonate (D) used in the present invention include sodium carbonate, sodium hydrogen carbonate, potassium carbonate, potassium hydrogen carbonate, calcium carbonate, magnesium carbonate, and sodium sesquicarbonate. These carbonates may be used alone or in combination of two or more thereof.

A content of the carbonate (D) in the solid composition of the present invention is 2% or more, preferably 3% or more, more preferably 10% or more from the viewpoint of physical properties and is 20% or less, preferably 19.5% or less, more preferably 14% or less from the viewpoint of taste and flavor. Additionally, the content is from 2 to 20%, preferably from 3 to 19.5%, more preferably from 10 to 14%.

The organic acid (E) used in the present invention is edible acids, and examples thereof include organic acid such as citric acid, succinic acid, ascorbic acid, acetic acid, gluconic acid, malic acid, tartaric acid, fumaric acid, and adipic acid. These organic acids may be used alone or in combination of two or more thereof. Among them, citric acid and malic acid are preferred, with citric acid being more preferred from the viewpoints that sticky texture and sticking to the mouth during eating are less and generated bubbles have good texture.

A content of the organic acid (E) in the solid composition of the present invention is 2% or more, preferably 2.5% or more, more preferably 3% or more, even more preferably 8% or more from the viewpoint of physical properties and is 18% or less, preferably 15% or less, more preferably 12% or less, even more preferably 11% or less from the viewpoints of taste and flavor. Additionally, the content is from 2 to 18%, preferably from 2.5 to 15%, more preferably from 3 to 12%, even more preferably from 8 to 11%.

In the solid composition of the present invention, a content mass ratio of the wheat albumin (A) to the carbonate (D), [(A)/(D)], is 1.5 or more, preferably 2.5 or more, more preferably 2.6 or more, even more preferably 3 or more from the viewpoints of suppressing sticky texture and sticking to the mouth during eating, reducing the bad taste characteristic to wheat albumin, suppressing bad returning odor, and providing good taste and flavor and is 16.5 or less, preferably 15.5 or less, more preferably 12 or less, even more preferably 5 or less. Additionally, the ratio is from 1.5 to 16.5, preferably from 2.5 to 15.5, more preferably from 2.6 to 12, even more preferably from 3 to 5.

A content mass ratio of the 0.19-wheat albumin (a) to the carbonate (D), [(a)/(D)], is 0.2 or more, preferably 0.3 or more, more preferably 0.35 or more, even more preferably 0.5 or more and is 4.1 or less, preferably 3.8 or less, more preferably 3 or less, even more preferably 2 or less, from the viewpoints of suppressing sticky texture and sticking to the mouth during eating and reducing the bad taste characteristic to wheat albumin. Additionally, the ratio is from 0.2 to 4.1, preferably from 0.3 to 3.8, more preferably from 0.35 to 3, even more preferably from 0.5 to 2.

Furthermore, in the solid composition of the present invention, the equivalent ratio of the organic acid (E) to the carbonate (D), [equivalent of (E)/equivalent of (D)], is 0.7 or more, preferably 0.8 or more, more preferably 0.85 or more, even more preferably 0.9 or more and is 1.9 or less, preferably 1.8 or less, more preferably 1.2 or less, even more preferably 1.1 or less, from the viewpoint of providing good balance in taste and flavor without prominent harshness derived from the carbonate and acid taste of the organic acid. Additionally, the ratio is from 0.7 to 1.9, preferably from 0.8 to 1.8, more preferably from 0.85 to 1.5, even more preferably from 0.9 to 1.2.

In the present invention, the term "equivalent ratio" refers to the value obtained by dividing the equivalent of the organic acid (E) by the equivalent of the carbonate (D) in the solid composition.

In addition to the above-described components, the solid composition of the present invention may appropriately contained therein a mineral (for example, calcium, magnesium, iron, zinc, chromium, selenium, manganese, molybdenum, copper, iodine, phosphorus, potassium, and sodium); a vitamin (for example, vitamin A, vitamin B1, vitamin B2, vitamin B6, vitamin B12, vitamin C, vitamin E, and folic acid, and salts or esters thereof); a sweetener (for example, a monosaccharide such as fructose, glucose, galactose, xylose, and tagatose, for example, an oligosaccharide such as sucrose, lactose, maltose, trehalose, isomaltooligosaccharide, galactooligosaccharide, fructooligosaccharide, lactosucrose, soy oligosaccharide, isomaltulose, and coupling sugar, for example, a sugar alcohol other than those having 6 to 12 carbon atoms, and for example, a synthetic sweetener such as saccharin, sucralose, and acesulfame potassium); an acidulant other than the organic acid (E), a flavor, a coloring agent, a preservative, or other additives, to the extent that the effects of the present invention is not impaired.

The form of the solid composition of the present invention is not particularly limited as long as it is a solid, for example, at room temperature (15 to 25° C.) Examples of the form include capsules, granules, powders, tablets, and pills. Among them, tablets are preferred from the viewpoint of capable of ingesting a small amount of the composition at a time, and chewable tablets are more preferred from the viewpoint of ease of ingestion.

The solid composition of the present invention containing a carbonate (D) and an organic acid (E) generates carbon dioxide gas in the mouth or in the presence of water.

In order to prepare the composition into such a dosage form, according to need, an appropriate combination of additives can be used. The additives include, for example, an excipient such as lactose, starches, crystalline cellulose, sucrose, mannitol, light anhydrous silicic acid, and calcium hydrogen phosphate; a binder such as hydroxypropyl methylcellulose, hydroxypropylcellulose, gelatin, pregelatinized starch, polyvinyl pyrrolidone, polyvinyl alcohol, pullulan, methyl cellulose, and hydrogenated oil; a disintegrator such as carmellose, carmellose calcium, croscarmellose sodium, crospovidone, corn starch, and low substituted hydroxypropylcellulose; a lubricant such as calcium stearate, magnesium stearate, sucrose fatty acid ester, sodium stearyl fumarate, talc, and silicon dioxide; a corrigent such as stevia and aspartame; a flavor; a bulking filler; a surfactant; a dispersing agent; a buffer; a preservative; a coating; and diluents, etc.

The solid composition of the present invention can be produced by a common method without particular limitation. For example, the composition can be produced by preparing a mixture of the wheat albumin (A), the alanine or a salt thereof (B), and optional additives, and subsequently subjecting the mixture to compression molding.

For example, in production of a tablet, a raw material may be directly compressed and molded (direct powder compression method) or a raw material may be granulated through, for example, dry granulation method or wet granulation method, followed by compressing and molding the granules (granule compression method). Among them, from the viewpoint of easiness of the process, the tablet is preferably formed by direct powder compression method.

In production of a tablet by direct compression, a tableting machine that is commonly used, such as a rotary tableting machine or a single punch tableting machine, may be used.

In production of a tablet from granules, the granules are produced by, for example, extruding granulation method using a basket granulator, a spheronization machine, a pelleter, etc., crushing granulation using a speed mill, a power mill, etc., oscillating granulation, agitating granulation, or fluidized bed granulation, and the granulated products are dried and regulated in size. The resulting granulated products are compressed into a tablet with the abovementioned tableting machine. The granulated products preferably have an average particle diameter of from 45 to 850 μm, more preferably from 100 to 500 μm.

The tablet may be a round tablet or an odd-shaped tablet having, for example, elliptic, oval, or square faces.

In addition, the compression molding pressure during tableting is 100 to 3000 kg/cm$^2$ from the viewpoints of maintaining the hardness, the disintegration, etc. of molded products.

Furthermore, the weight of each tablet of the present invention is 0.1 to 2 g, preferably 0.5 to 1.8 g, and more preferably 0.8 to 1.5 g from the viewpoints of ease and effectiveness.

Regarding the above-described embodiment, the present invention further discloses the following compositions.

[1] A solid composition comprising the following components (A) and (B):
(A) wheat albumin, and
(B) alanine or a salt thereof, wherein
a mass ratio of a content of the 0.19-wheat albumin (a) in the solid composition to a content of the alanine or a salt thereof in terms of alanine (b) in the solid composition, [(a):(b)], is 250:1 to 10:1.

[2] The solid composition according to aspect [1], wherein a content of the wheat albumin (A) in the solid composition is preferably 10% by mass or more, more preferably 20% by mass or more, still more preferably 30% by mass or more, and preferably 70% by mass or less, more preferably 60% by mass or less, still more preferably 55% by mass or less, still more preferably 50% by mass, and the content is preferably from 10 to 70% by mass, more preferably from 20 to 70% by mass, still more preferably from 30 to 60% by mass, still more preferably from 30 to 55% by mass, still more preferably from 30 to 50% by mass.

[3] The solid composition according to aspect [1] or [2], wherein the wheat albumin (A) contains 0.19-wheat albumin (a), a content of the 0.19-wheat albumin (a) in the wheat albumin (A) is preferably 10% by mass or more, more preferably 15% by mass or more, still more preferably 20% by mass or more, still more preferably 25% by mass or more, and preferably 60% by mass or less, more preferably 40% by mass or less, still more preferably 35% by mass or less, still more preferably 31% by mass or less, and the content is preferably from 10 to 60% by mass, more preferably from 15 to 40% by mass, still more preferably from 20 to 35% by mass, still more preferably from 25 to 31% by mass.

[4] The solid composition according to any one of aspects [1] to [3], wherein a content of the 0.19-wheat albumin in the solid composition is preferably 2% by mass or more, more preferably 7% by mass or more, still more preferably 7.5% by mass or more, and preferably 18% by mass or less, more preferably 15% by mass or less, still more preferably 13% by mass or less, and the content is preferably from 2 to 18% by mass, more preferably from 7 to 15% by mass, still more preferably from 7.5 to 13% by mass.

[5] The solid composition according to any one of aspects [1] to [4], wherein a content of the alanine or a salt thereof (B) in the solid composition is, in terms of alanine, preferably 0.02% by mass or more, more preferably 0.04% by mass or more, and still preferably 0.05% by mass or more, and preferably 2.5% by mass or less, more preferably 1.2% by mass or less, still more preferably 0.6% by mass or less, still more preferably 0.2% by mass or less.

[6] The solid composition according to any one of aspects [1] to [5], wherein a content of the 0.19-wheat albumin (a) in the solid composition based on the content of the alanine or a salt thereof in terms of alanine (b) in the solid composition defined as 1 is preferably 250 or less, more preferably 150 or less, still more preferably 100 or less, still more preferably 95 or less, still more preferably 90 or less, and preferably 10 or more, more preferably 20 or more, still more preferably 30 or more, still more preferably 50 or more, still more preferably 75 or more.

[7] The solid composition according to any one of aspects [1] to [5], wherein a mass ratio of a content of the 0.19-wheat albumin (a) in the solid composition to a content of the alanine or a salt thereof in terms of alanine (b) in the solid composition, [(a):(b)], is preferably from 150:1 to 20:1, more preferably from 100:1 to 30:1, still more preferably from 95:1 to 50:1, still more preferably from 90:1 to 75:1.

[8] The solid composition according to any one of aspects [1] to [7], further comprising a sugar alcohol having 6 to 12 carbon atoms (C).

[9] The solid composition according to aspect [8], wherein the sugar alcohol having 6 to 12 carbon atoms (C) is preferably one or more selected from the group consisting of maltitol, sorbitol, lactitol, and mannitol, more preferably one or more selected from the group consisting of maltitol, sorbitol, and lactitol, still more preferably maltitol, sorbitol, or a combination thereof, still more preferably maltitol.

[10] The solid composition according to aspect [8] or [9], wherein a content mass ratio of the sugar alcohol having 6 to 12 carbon atoms (C) to the wheat albumin (A), [(C)/(A)], in the solid composition is preferably 0.2 or more, more preferably 0.4 or more, still more preferably 0.5 or more, still more preferably 0.7 or more, and preferably 10 or less, more preferably 7 or less, still more preferably 5 or less, still more preferably 2 or less, still more preferably 1.9 or less, still more preferably 1 or less, and the ratio is preferably from 0.2 to 10, more preferably from 0.4 to 7, still more preferably from 0.4 to 5, still more preferably from 0.5 to 2, still more preferably from 0.7 to 1.9, still more preferably from 0.7 to 1.

[11] The solid composition according to any one of aspects [8] to [10], wherein a content mass ratio of the sugar alcohol having 6 to 12 carbon atoms (C) to the 0.19-wheat albumin (a), [(C)/(a)], in the solid composition is preferably 0.8 or more, more preferably 1.5 or more, still more preferably 2.5 or more, and, preferably 10 or less, more preferably 7.5 or less, still more preferably 5 or less, still more preferably 3.5 or less.

[12] The solid composition according to any one of aspects [8] to [11], wherein a content of the sugar alcohol having 6 to 12 carbon atoms (C) in the solid composition is preferably 10% by mass or more and more preferably 20% by mass or more, and preferably 90% by mass or less, more preferably 65% by mass or less, still more preferably 60% by mass or less, still more preferably 55% by mass or less, still preferably 40% by mass or less, and the content is preferably from 10 to 90% by mass, more preferably from 20 to 65% by mass, still more preferably from 20 to 60% by mass, still more preferably from 20 to 55% by mass, still more preferably from 20 to 40% by mass.

[13] The solid composition according to any one of aspects [1] to [12], further comprising a carbonate (D) and an organic acid (E).

[14] The solid composition according to aspect [13], wherein the carbonate (D) is preferably one or more selected from the group consisting of sodium carbonate, sodium hydrogen carbonate, potassium carbonate, potassium hydrogen carbonate, calcium carbonate, magnesium carbonate, and sodium sesquicarbonate.

[15] The solid composition according to aspect [13] or [14], wherein the organic acid (E) is preferably one or more selected from the group consisting of citric acid, succinic acid, ascorbic acid, acetic acid, gluconic acid, malic acid, tartaric acid, fumaric acid, and adipic acid, more preferably citric acid, malic acid, or combination thereof, still more preferably citric acid.

[16] The solid composition according to any one of aspects [13] to [15], wherein a content mass ratio of the wheat albumin (A) to the carbonate (D) in the solid composition, [(A)/(D)], is preferably 1.5 or more, more preferably 2.5 or more, still more preferably 2.6 or more, still more preferably 3 or more, and preferably 16.5 or less, more preferably 15.5 or less, still more preferably 12 or less, still more preferably 5 or less, and the ratio is preferably from 1.5 to 16.5, more preferably from 2.5 to 15.5, even more preferably 2.6 to 12, and still more preferably 3 to 5.

[17] The solid composition according to any one of aspects [13] to [16], wherein a content mass ratio of the 0.19-wheat albumin (a) to the carbonate (D), [(a)/(D)], in the solid composition is preferably 0.2 or more, more preferably 0.3 or more, still more preferably 0.35 or more, still more preferably 0.5 or more, and preferably 4.1 or less, more preferably 3.8 or less, still more preferably 3 or less, still more preferably 2 or less, and the content is preferably from 0.2 to 4.1, more preferably from 0.3 to 3.8, still more preferably from 0.35 to 3, still more preferably from 0.5 to 2.

[18] The solid composition according to any one of aspects [13] to [17], wherein an equivalent ratio of the organic acid (E) to the carbonate (D), [equivalent of (E)/equivalent of (D)], is preferably 0.7 or more, more preferably 0.8 or more, still more preferably 0.85 or more, still more preferably 0.9 or more, and preferably 1.9 or less, more preferably 1.8 or less, still more preferably 1.2 or less, still more preferably 1.1 or less, and the ratio is preferably from 0.7 to 1.9, more preferably from 0.8 to 1.8, still more preferably from 0.85 to 1.5, and still more preferably from 0.9 to 1.2.

[19] The solid composition according to any one of aspects [1] to [18], wherein the solid composition is a chewable tablet.

EXAMPLES

Raw Materials

Wheat albumin: wheat albumin NA-1, Nisshin Pharma Inc. (0.19-wheat albumin content: 25%)
DL-Alanine: DL-alanine, KYOWA HAKKO BIO CO., LTD.
Maltitol: powder maltitol G3, Mitsubishi Shoji Foodtech Co., Ltd.
Sorbitol: Sorbitol TBS, B Food Science Co., Ltd.
Sodium hydrogen carbonate: sodium hydrogen carbonate, Wako Pure Chemical Industries, Ltd.
Citric acid: citric acid anhydride 80MP, FUSO CHEMICAL CO., LTD.
Malic acid: DL-malic acid, FUSO CHEMICAL CO., LTD.

Analysis of Alanine 50 mg of the solid composition was dissolved in 1 g of distilled water and centrifuged by using a centrifuge under conditions of 3000 rpm at 25° C. for 10 minutes. After 500 μL of 5% trichloroacetic acid was added to the 500 μL of the supernatant, the mixture was centrifuged by using a centrifuge under conditions of 10000 r/min at 5° C. for 10 minutes. After 500 μL of the supernatant was diluted with 0.02 N hydrochloric acid to 2 to 10 folds, the diluted supernatant was filtered through a 0.2 μm filter and used as a sample. The sample was analyzed in an amino acid analyzer (Hitachi L-8800).

Analysis of Carbonate

The carbonate content in a solid composition is analyzed as follows.

In a container, 0.1 to 0.2 g of a solid composition is weighed, and 10 mL of water and 2 mL of 50% phosphoric acid are added thereto. The container is sealed, and the mixture is sonicated for 10 minutes and is subsequently left to stand for 1 hour. The head-space gas is subjected to gas chromatography to determine the amount of $CO_2$, and the carbonate content is determined from the amount of $CO_2$ generated.

Gas Chromatography Operating Conditions

Model: GC-14B (Shimadzu Corporation)
Detector: TCD
Column: Chromosorb 101, 80 to 100 mesh, glass tube: φ3.2 mm×2 m
Temperature: column: 50° C., inlet and detector: 100° C.
Cell electric current: 75 mA
Gas pressure: helium (carrier gas): 100 kPa
Injection volume: head-space gas: 0.2 mL Analysis of Organic Acid The organic acid content in a solid composition is analyzed as follows.

1 g of a solid composition is weighed, and 20 mL of 5% perchloric acid is added thereto. The resulting mixture is shaken for 10 minutes for extraction. The volume is adjusted to 200 mL with water, and sonication is performed for 10 minutes. After filtration, the resulting sample is subjected to high-performance liquid chromatography.

High-Performance Liquid Chromatography Operating Conditions

Model: LC-20AD (Shimadzu Corporation)
Detector: ultraviolet and visible spectrophotometer SPD-20AV (Shimadzu Corporation)
Column temperature: 40° C.
Mobile phase: 3 mmol/L perchloric acid Reaction solution: 15 mmol/L disodium hydrogen phosphate solution containing 0.2 mmol/L bromothymol blue
Flow rate: mobile phase: 1.0 mL/min, reaction solution: 1.4 mL/min
Measurement wavelength: 445 nm Preparation of Chewable Tablet Examples 1 to 11 and Comparative Examples 1 to 5

Raw material components were mixed based on the blending compositions shown in Table 1. Subsequently, each mixture was compressed into a tablet having a weight of 1000 mg using a single punch tableting machine (manufactured by Riken Seiki Co., Ltd.) with a ring-form punch having a hole diameter of 13 mm to obtain a chewable tablet. The contents of 0.19-wheat albumin (a) and the alanine (b) in the chewable tablet are shown in Table 1.

The resulting inventive products and comparative products were subjected to sensory evaluation. The evaluation was performed by three specialized panelists for the taste and flavor characteristic to wheat albumin (the bad taste and offensive odor) and the taste derived from the added amino acid in accordance with the evaluation criteria shown below, and average values were used as marks. The results are shown in Table 1.

[Taste and Flavor Characteristic to Wheat Albumin]
5: No bad taste and offensive odor are sensed.
4: Bad taste and offensive odor are hardly sensed.
3: Bad taste and offensive odor are slightly sensed.
2: Bad taste and offensive odor are strongly sensed.
1: Bad taste and offensive odor are very strongly sensed.

[Taste Derived from the Added Amino Acid]
5: No taste derived from the added amino acid is sensed with no uncomfortable taste and flavor.
4: The taste of the added amino acid is hardly sensed.
3: The taste of the added amino acid is slightly sensed.
2: The taste of the added amino acid is strongly sensed.
1: The taste of the added amino acid is very strongly sensed.

TABLE 1

| | | Example 1 | Example 2 | Example 3 | Example 4 | Example 5 | Example 6 | Example 7 | Example 8 | Example 9 |
|---|---|---|---|---|---|---|---|---|---|---|
| Composition (% by mass) | (A) Wheat albumin | 50 | 50 | 50 | 50 | 50 | 20 | 20 | 30 | 30 |
| | (B) DL-Alanine | 0.01 | 0.05 | 0.1 | 0.5 | 1 | 0.01 | 0.04 | 0.02 | 0.07 |
| | Sodium glutamate | 0 | 0 | 0 | 0 | 0 | 0 | 0 | 0 | 0 |
| | Corn starch | 47.99 | 47.95 | 47.9 | 47.5 | 47 | 77.99 | 77.96 | 67.98 | 67.93 |
| | Calcium stearate | 2 | 2 | 2 | 2 | 2 | 2 | 2 | 2 | 2 |
| | Total | 100.0 | 100.0 | 100.0 | 100.0 | 100.0 | 100.0 | 100.0 | 100.0 | 100.0 |
| Content of 0.19-wheat albumin (a)(% by mass) | | 12.5 | 12.5 | 12.5 | 12.5 | 12.5 | 5 | 5 | 7.5 | 7.5 |
| Content of alanine (b)(% by mass) | | 0.051 | 0.091 | 0.141 | 0.541 | 1.041 | 0.026 | 0.056 | 0.045 | 0.095 |
| (a)/(b) Mass ratio | | 245 | 137 | 89 | 23 | 12 | 189 | 89 | 168 | 79 |
| Evaluation items | Taste and Flavor characteristic to wheat albumin | 3 | 4 | 5 | 5 | 5 | 4 | 5 | 3 | 5 |
| | Taste derived from the added amino acid | 5 | 5 | 5 | 4 | 3 | 5 | 5 | 5 | 5 |

TABLE 1-continued

|  |  | Example 10 | Example 11 | Comparative Example 1 | Comparative Example 2 | Comparative Example 3 | Comparative Example 4 | Comparative Example 5 |
|---|---|---|---|---|---|---|---|---|
| Composition (% by mass) | (A) Wheat albumin | 60 | 60 | 50 | 50 | 50 | 50 | 30 |
|  | (B) DL-Alanine | 0.05 | 0.13 | 0 | 0.001 | 3 | 0 | 0 |
|  | Sodium glutamate | 0 | 0 | 0 | 0 | 0 | 0.1 | 0 |
|  | Corn starch | 37.95 | 37.87 | 48 | 47.999 | 45 | 47.9 | 68 |
|  | Calcium stearate | 2 | 2 | 2 | 2 | 2 | 2 | 2 |
|  | Total | 100.0 | 100.0 | 100.0 | 100.0 | 100.0 | 100.0 | 100.0 |
| Content of 0.19-wheat albumin (a)(% by mass) |  | 15 | 15 | 12.5 | 12.5 | 12.5 | 12.5 | 7.5 |
| Content of alanine (b)(% by mass) |  | 0.099 | 0.179 | 0.041 | 0.042 | 3.041 | 0.041 | 0.025 |
| (a)/(b) Mass ratio |  | 151 | 84 | 305 | 298 | 4 | 305 | 305 |
| Evaluation items | Taste and Flavor characteristic to wheat albumin | 3 | 5 | 1 | 2 | 5 | 1 | 2 |
|  | Taste derived from the added amino acid | 5 | 5 | 5 | 5 | 2 | 5 | 5 |

As obvious from Table 1, in the inventive products, as compared with the comparative products, reduction in the taste and flavor characteristic to wheat albumin (the bad taste and offensive odor) was confirmed, no taste derived from the added amino acid was sensed, and a good taste and flavor was provided. On the contrary, in Comparative Example 4, in which a certain amount of sodium glutamate was blended instead of alanine, the taste and flavor characteristic to wheat albumin was strong, delicious taste derived from glutamic acid was also strongly sensed, and the balance in taste and flavor was bad.

Preparation of a Chewable Tablet

Examples 12 to 17

Chewable tablets were prepared in the same manner as in Example 1 except that raw material components were mixed based on the blending compositions shown in Table 2. The contents of the 0.19-wheat albumin (a) and the alanine (b) in the chewable tablet are shown in Table 2.

The resulting inventive products were subjected to sensory evaluation. The evaluation was performed by three specialized panelists for the taste and flavor characteristic to wheat albumin (the bad taste and offensive odor) and the taste derived from the added amino acid in accordance with the above-described evaluation criteria. Additionally, the bad returning odor from the esophagus during/after ingestion was evaluated in accordance with the evaluation criteria shown below. In every evaluation, average values were used as marks. The results are shown in Table 2.

[Bad Returning Odor]
3: No bad returning odor is sensed.
2: Bad returning odor is slightly sensed.
1: Bad returning odor is strongly sensed.

TABLE 2

|  |  | Example 12 | Example 13 | Example 14 | Example 15 | Example 16 | Example 17 |
|---|---|---|---|---|---|---|---|
| Composition (% by mass) | (A) Wheat albumin | 40 | 40 | 40 | 40 | 40 | 50 |
|  | (B) DL-Alanine | 0.1 | 0.1 | 0.1 | 0.1 | 0.1 | 0.1 |
|  | (C) Maltitol | 0 | 10 | 20 | 30 | 0 | 35 |
|  | (C) Sorbitol | 0 | 0 | 0 | 0 | 30 | 0 |
|  | Corn starch | 57.9 | 47.9 | 37.9 | 27.9 | 27.9 | 12.9 |
|  | Calcium stearate | 2 | 2 | 2 | 2 | 2 | 2 |
|  | Total | 100.0 | 100.0 | 100.0 | 100.0 | 100.0 | 100.0 |
| Content of 0.19-wheat albumin (a)(% by mass) |  | 10 | 10 | 10 | 10 | 10 | 12.5 |
| Content of alanine (b)(% by mass) |  | 0.133 | 0.133 | 0.133 | 0.133 | 0.133 | 0.141 |
| (a)/(b) Mass ratio |  | 75 | 75 | 75 | 75 | 75 | 89 |
| (C)/(A) Mass ratio |  | — | 0.25 | 0.5 | 0.75 | 0.75 | 0.7 |
| (C)/(a) Mass ratio |  | — | 1.0 | 2.0 | 3.0 | 3.0 | 2.8 |
| Evaluation items | Taste and Flavor characteristic to wheat | 5 | 5 | 5 | 5 | 5 | 5 |

TABLE 2-continued

|  | Example 12 | Example 13 | Example 14 | Example 15 | Example 16 | Example 17 |
|---|---|---|---|---|---|---|
| albumin |  |  |  |  |  |  |
| Taste derived from the added amino acid | 5 | 5 | 5 | 5 | 5 | 5 |
| Bad returning odor | 1 | 2 | 3 | 3 | 2 | 3 |

As obvious from Table 2, in the products further having a specific sugar alcohol blended therein in Examples 13 to 17, the offensive odor characteristic to wheat albumin is more reduced, and reduction in the bad returning odor was confirmed.

Preparation of a Chewable Tablet

Examples 18 to 29

Chewable tablets were prepared in the same manner as in Example 1 except that raw material components were mixed based on the blending compositions shown in Table 3. The contents of the 0.19-wheat albumin (a) and the alanine (b) in the chewable tablet are shown in Table 3.

The resulting inventive products were subjected to sensory evaluation. The evaluation was performed by three specialized panelists for the taste and flavor characteristic to wheat albumin (the bad taste and offensive odor), the taste derived from the added amino acid, and the bad returning odor from the esophagus during/after ingestion in accordance with the above-described evaluation criteria. Additionally, the sticking to the mouth during ingestion, the texture of bubbles, and balance in taste and flavor were evaluated in accordance with the evaluation criteria shown below. In every evaluation, average values were used as marks. The results are shown in Table 3.

[Sticking to the Mouth]
  3: Sticking to teeth or tongue is very weak.
  2: Sticking to teeth or tongue is weak.
  1: Sticking to teeth or tongue is strong.

[Texture of Bubbles]
  3: Bubbles in the mouth disappear very fast.
  2: Bubbles in the mouth disappear fast.
  1: Bubbles in the mouth disappear slowly.

[Balance in Taste and Flavor]
  3: Balance is very good without prominent taste and flavor of organic acid and carbonate.
  2: Balance is good without prominent taste and flavor of organic acid and carbonate.
  1: Balance is bad without prominent taste and flavor of organic acid and carbonate.

TABLE 3

|  |  | Example 18 | Example 19 | Example 20 | Example 21 | Example 22 | Example 23 | Example 24 | Example 26 | Example 27 | Example 28 | Example 29 |
|---|---|---|---|---|---|---|---|---|---|---|---|---|
| Composition (% by mass) | (A) Wheat albumin | 40 | 40 | 40 | 40 | 40 | 40 | 40 | 40 | 40 | 40 | 40 |
|  | (B) DL-Alanine | 0.1 | 0.1 | 0.1 | 0.1 | 0.1 | 0.1 | 0.1 | 0.1 | 0.1 | 0.1 | 0.1 |
|  | (C) Maltitol | 0 | 0 | 0 | 0 | 0 | 0 | 0 | 0 | 0 | 20 | 20 |
|  | (D) Sodium hydrogen carbonate | 0 | 12 | 12 | 12 | 14 | 15 | 8 | 4 | 4 | 12 | 11 |
|  | (E) Citric acid | 0 | 8 | 10.5 | 12 | 9 | 10 | 9 | 5 | 3 | 10.5 | — |
|  | (E) Malic acid | — | — | — | — | — | — | — | — | — | — | 10.5 |
|  | Corn starch | 57.9 | 37.9 | 35.4 | 33.9 | 34.9 | 32.9 | 40.9 | 48.9 | 50.9 | 15.4 | 12.9 |
|  | Calcium stearate | 2 | 2 | 2 | 2 | 2 | 2 | 2 | 2 | 2 | 2 | 2 |
|  | Total | 100.0 | 100.0 | 100.0 | 100.0 | 100.0 | 100.0 | 100.0 | 100.0 | 100.0 | 100.0 | 96.5 |
| Content of 0.19-wheat albumin (a)(% by mass) |  | 10.0 | 10.0 | 10.0 | 10.0 | 10.0 | 10.0 | 10.0 | 10.0 | 10.0 | 10.0 | 10.0 |
| Content of alanine (b)(% by mass) |  | 0.133 | 0.133 | 0.133 | 0.133 | 0.133 | 0.133 | 0.133 | 0.133 | 0.133 | 0.133 | 0.133 |
| (a)/(b) Mass ratio |  | 75 | 75 | 75 | 75 | 75 | 75 | 75 | 75 | 75 | 75 | 75 |
| (C)/(A) Mass ratio |  | — | — | — | — | — | — | — | — | — | 0.50 | 0.50 |
| (C)/(a) Mass ratio |  | — | — | — | — | — | — | — | — | — | 2.00 | 2.00 |
| (A)/(D) Mass ratio |  | — | 3.33 | 3.33 | 3.33 | 2.86 | 2.67 | 5.00 | 10.00 | 10.00 | 3.33 | 3.64 |
| (a)/(D) Mass ratio |  | — | 0.83 | 0.83 | 0.83 | 0.71 | 0.67 | 1.25 | 2.50 | 2.50 | 0.83 | 0.91 |
| (E)/(D) Equivalent ratio |  | — | 0.88 | 1.15 | 1.31 | 0.84 | 0.88 | 1.48 | 1.64 | 0.98 | 1.15 | 1.20 |
| Evaluation items | Taste and Flavor characteristic to wheat albumin | 5 | 5 | 5 | 5 | 5 | 5 | 5 | 5 | 5 | 5 | 5 |
|  | Taste derived from the added amino acid | 5 | 5 | 5 | 5 | 5 | 5 | 5 | 5 | 5 | 5 | 5 |

TABLE 3-continued

|  | Example 18 | Example 19 | Example 20 | Example 21 | Example 22 | Example 23 | Example 24 | Example 26 | Example 27 | Example 28 | Example 29 |
|---|---|---|---|---|---|---|---|---|---|---|---|
| Bad returning odor | 1 | 2 | 2 | 2 | 2 | 2 | 2 | 1 | 1 | 3 | 3 |
| Sticking to the mouth | 1 | 3 | 3 | 3 | 3 | 3 | 3 | 2 | 2 | 3 | 3 |
| Texture of bubbles | — | 2 | 3 | 3 | 3 | 2 | 2 | 2 | 2 | 3 | 3 |
| Balance in taste and flavor | 2 | 2 | 3 | 2 | 2 | 2 | 2 | 2 | 3 | 3 | 3 |

As obvious from Table 3, in the products further having a carbonate and an organic acid blended therein in Examples 19 to 29, the sticky texture and sticking to the mouth during eating were suppressed, the bad taste characteristic to wheat albumin was further reduced, the texture of bubbles was good, and the balance in taste and flavor was good.

What is claimed is:

1. A solid composition comprising the following components (A) and (B):
    (A) wheat albumin, and
    (B) alanine or a salt thereof,
    wherein a content of 0.19-wheat albumin (a) in the solid composition is from 2 to 18% by mass and a mass ratio of the content of the 0.19-wheat albumin (a) in the solid composition to the content of the alanine or a salt thereof in terms of alanine (b) in the solid composition, [(a):(b)], is from 250:1 to 10:1.

2. The solid composition according to claim 1, wherein the content of the alanine or a salt thereof (B) in the solid composition is from 0.02 to 2.5% by mass in terms of alanine.

3. The solid composition according to claim 1, wherein the content of the alanine or a salt thereof (B) in the solid composition is from 0.04 to 1.2% by mass in terms of alanine.

4. The solid composition according to claim 1, wherein the content of 0.19-wheat albumin (a) in the solid composition is from 7 to 15% by mass.

5. The solid composition according to claim 1, wherein the content of the wheat albumin (A) in the solid composition is from 30 to 60% by mass.

6. The solid composition according to claim 1, wherein the content of the wheat albumin (A) in the solid composition is from 30 to 50% by mass.

7. The solid composition according to claim 1, wherein the mass ratio of the content of the 0.19-wheat albumin (a) in the solid composition to the content of the alanine or a salt thereof in terms of alanine (b) in the solid composition, [(a):(b)], is from 150:1 to 20:1.

8. The solid composition according to claim 1, wherein the mass ratio of the content of the 0.19-wheat albumin (a) in the solid composition to the content of the alanine or a salt thereof in terms of alanine (b) in the solid composition, [(a):(b)], is from 100:1 to 30:1.

9. The solid composition according to claim 1, wherein the mass ratio of the content of the 0.19-wheat albumin (a) in the solid composition to the content of the alanine or a salt thereof in terms of alanine (b) in the solid composition, [(a):(b)], is from 90:1 to 75:1.

10. The solid composition according to claim 1, further comprising a sugar alcohol having 6 to 12 carbon atoms (C), wherein a content mass ratio of the sugar alcohol having 6 to 12 carbon atoms (C) to the wheat albumin (A), [(C)/(A)], in the solid composition is 0.2 or more.

11. The solid composition according to claim 1, further comprising a sugar alcohol having 6 to 12 carbon atoms (C), wherein a content mass ratio of the sugar alcohol having 6 to 12 carbon atoms (C) to the wheat albumin (A), [(C)/(A)], in the solid composition is from 0.2 to 10.

12. The solid composition according to claim 1, further comprising a sugar alcohol having 6 to 12 carbon atoms (C), wherein a content mass ratio of the sugar alcohol having 6 to 12 carbon atoms (C) to the wheat albumin (A), [(C)/(A)], in the solid composition is from 0.4 to 5.

13. The solid composition according to claim 1, further comprising a carbonate (D) and an organic acid (E).

14. The solid composition according to claim 13, wherein the carbonate (D) is at least one selected from the group consisting of sodium carbonate, sodium hydrogen carbonate, potassium carbonate, potassium hydrogen carbonate, calcium carbonate, magnesium carbonate, and sodium sesquicarbonate.

15. The solid composition according to claim 13, wherein the organic acid (E) is at least one selected from the group consisting of citric acid, succinic acid, ascorbic acid, acetic acid, gluconic acid, malic acid, tartaric acid, fumaric acid, and adipic acid.

16. The solid composition according to claim 1, further comprising a carbonate (D), wherein a content mass ratio of the wheat albumin (A) to the carbonate (D), [(A)/(D)], in the solid composition is from 1.5 to 16.5.

17. The solid composition according to claim 16, further comprising an organic acid (E), wherein an equivalent ratio of the organic acid (E) to the carbonate (D), [equivalent (E)/equivalent (D)], is from 0.7 to 1.9.

18. The solid composition according to claim 1, wherein the solid composition is a chewable tablet.

19. A solid composition comprising the following components (A) and (B):
    (A) from 20 to 70% by mass of wheat albumin, and
    (B) alanine and a salt thereof,
    wherein a content of 0.19-wheat albumin (a) in the solid composition is from 2 to 18% by mass and a mass ratio of the content of the 0.19-wheat albumin (a) in the solid composition to a content of the alanine or a salt thereof in terms of alanine (b) in the solid composition, [(a):(b)], is from 250:1 to 10:1.

20. A solid composition comprising the following components (A) and (B):
    (A) from 20 to 60% by mass of wheat albumin, and
    (B) alanine and a salt thereof,
    wherein a content of 0.19-wheat albumin (a) in the solid composition is from 7 to 15% by mass and a mass ratio of the content of the 0.19-wheat albumin (a) in the solid composition to a content of the alanine or a salt thereof in terms of alanine (b) in the solid composition, [(a):(b)], is from 250:1 to 10:1.

* * * * *